United States Patent
Kitano et al.

(10) Patent No.: US 12,403,209 B2
(45) Date of Patent: Sep. 2, 2025

(54) DECONTAMINATION DEVICE

(71) Applicant: AIREX CO., LTD., Nagoya (JP)

(72) Inventors: Tsukasa Kitano, Nagoya (JP); Zhiqiang Guo, Nagoya (JP); Kazuhiko Kitahora, Nagoya (JP); Yoshitaka Ogata, Nagoya (JP); Daisuke Kakuda, Nagoya (JP); Yoshiaki Okada, Nagoya (JP); Koji Kawasaki, Nagoya (JP)

(73) Assignee: AIREX CO., LTD. (JP)

( * ) Notice: Subject to any disclaimer, the term of this patent is extended or adjusted under 35 U.S.C. 154(b) by 173 days.

(21) Appl. No.: 17/911,802

(22) PCT Filed: Nov. 4, 2021

(86) PCT No.: PCT/JP2021/040571
§ 371 (c)(1),
(2) Date: Sep. 15, 2022

(87) PCT Pub. No.: WO2022/158084
PCT Pub. Date: Jul. 28, 2022

(65) Prior Publication Data
US 2023/0347002 A1  Nov. 2, 2023

(30) Foreign Application Priority Data

Jan. 21, 2021 (JP) ................ 2021-007769

(51) Int. Cl.
*A61L 2/22* (2006.01)
*A61L 2/26* (2006.01)

(52) U.S. Cl.
CPC ........ *A61L 2/22* (2013.01); *A61L 2/26* (2013.01); *A61L 2202/122* (2013.01); *A61L 2202/15* (2013.01)

(58) Field of Classification Search
None
See application file for complete search history.

(56) References Cited

U.S. PATENT DOCUMENTS

2022/0184259 A1* 6/2022 Kawasaki ............. B06B 1/0607

FOREIGN PATENT DOCUMENTS

| JP | 2003002196 A | 1/2003 |
| JP | 2006198120 A | 8/2006 |

(Continued)

OTHER PUBLICATIONS

PCT International Search Report and Written Opinion, PCT/JP2021/040571, Dec. 28, 2021, 8 pages [Includes English language translation of International Search Report].

*Primary Examiner* — Jelitza M Perez
(74) *Attorney, Agent, or Firm* — Quarles & Brady LLP; Yakov S. Sidorin

(57) ABSTRACT

A decontamination device capable of confirming accurate operations of a mist circulation dispersion means before and after or during a decontamination operation and guaranteeing the overall operation as a decontamination device. The device includes a mist supply means, a mist circulation dispersion means, and an ultrasonic detection means. The mist supply means converts a chemical for decontamination of the inside of a working chamber of the device into a mist for decontamination and supplies such mist to the inside of the working chamber. The mist circulation dispersion means subjects a vibrating board (which includes a plurality of ultrasonic transmitters) to ultrasonic vibration to generate sound flows with ultrasound from board surfaces in the vertical direction and presses the mist with acoustic radiation pressure of the sound flows in order to circulate and disperse the mist for decontamination in the working chamber. The ultrasonic detection means includes an ultrasonic receiver configured to detect the operation of the plurality of ultrasonic transmitters included in the vibrating board in as a whole and/or the operation of each of the constituent ultrasonic transmitters.

4 Claims, 5 Drawing Sheets

(56) References Cited

FOREIGN PATENT DOCUMENTS

| JP | 2020156970 A | 10/2020 | | |
| WO | WO-2020196036 A1 | * | 10/2020 | ............. A61L 2/025 |

* cited by examiner

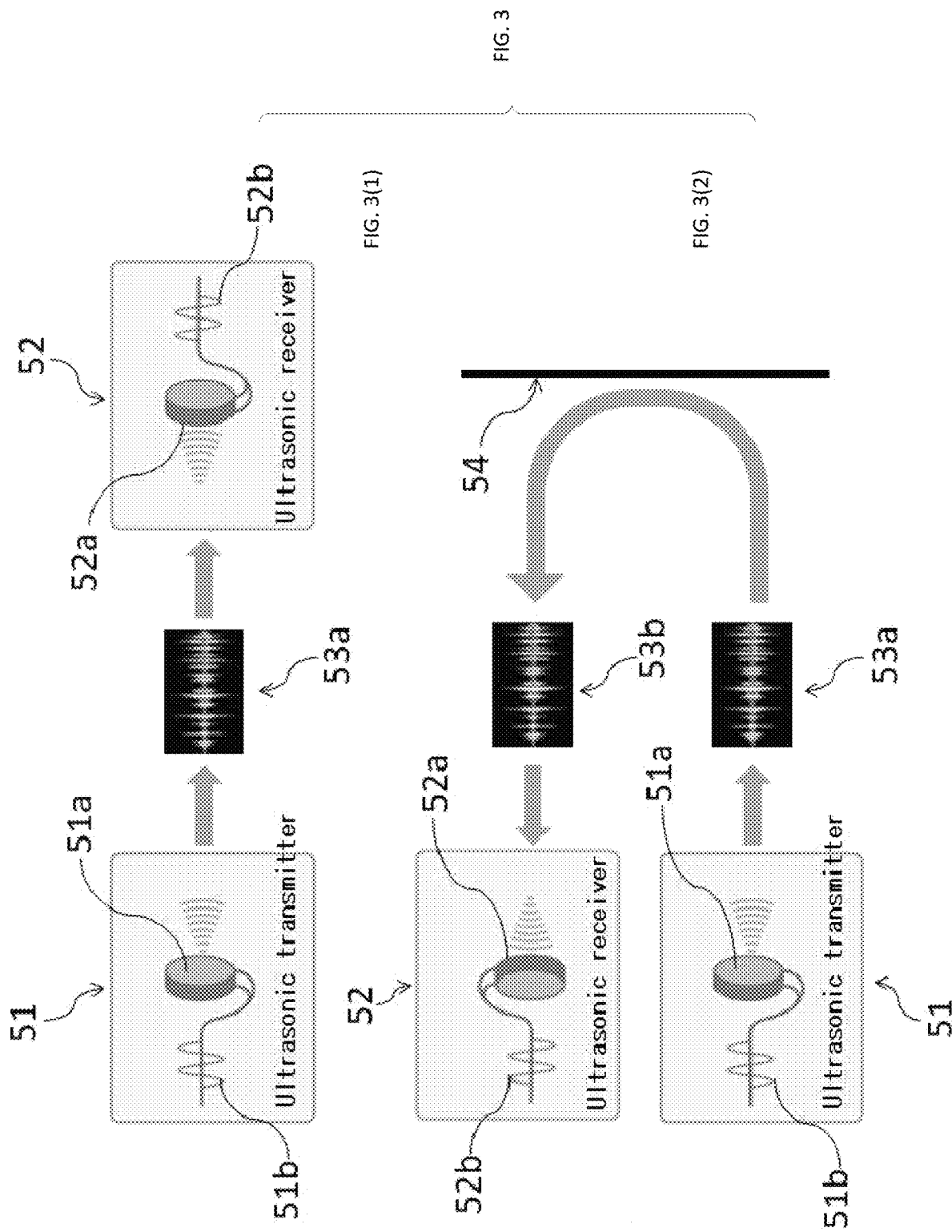

FIG. 5
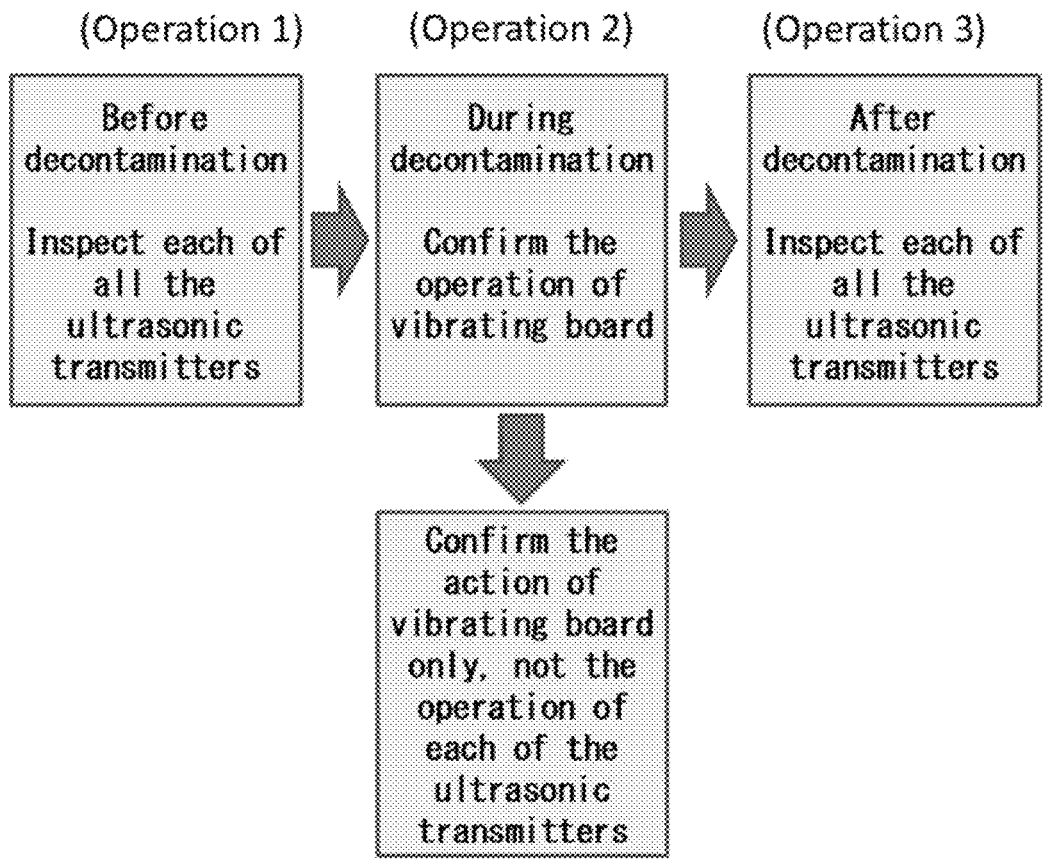
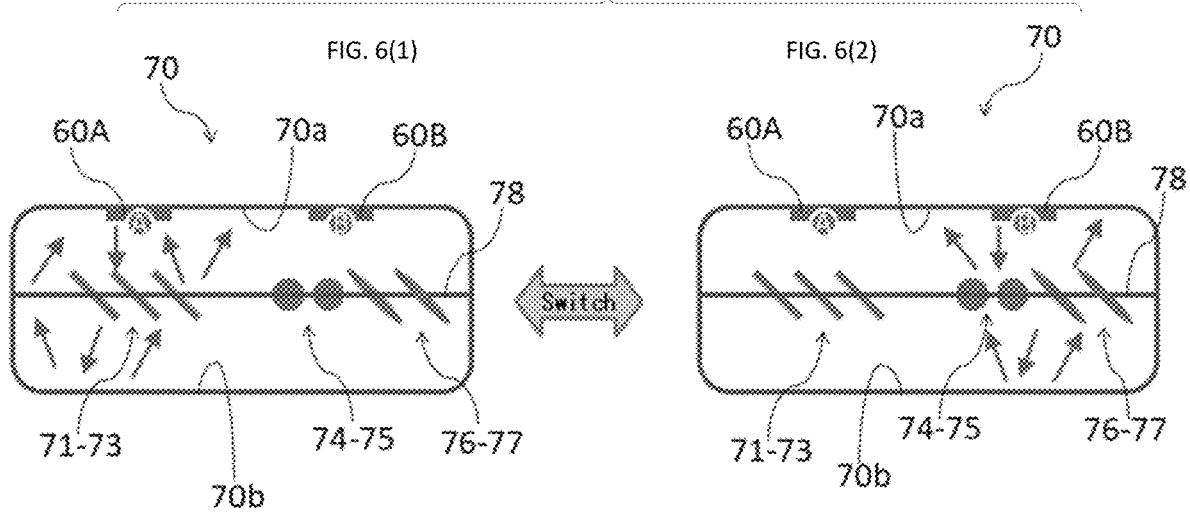

FIG. 7
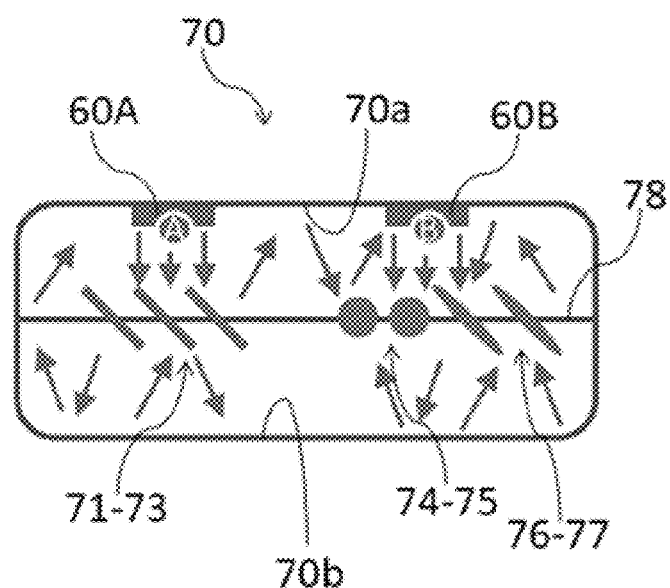
FIG. 8
FIG. 8(1)
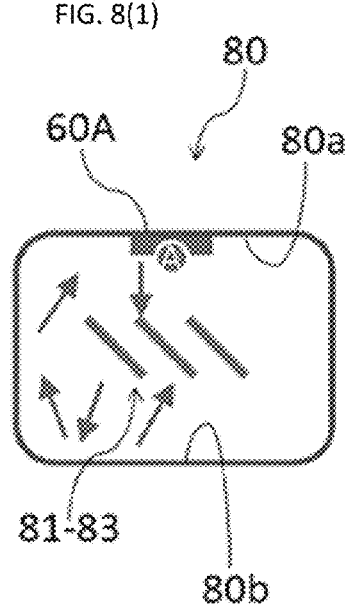
FIG. 8(2)
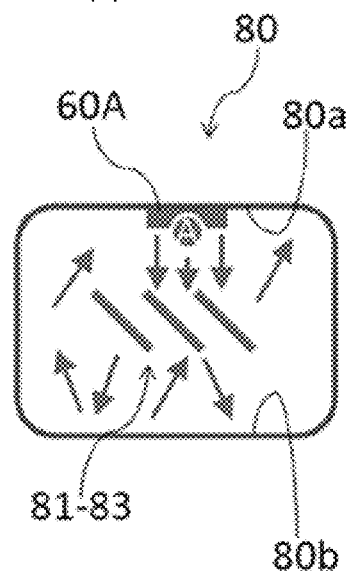

DECONTAMINATION DEVICE

CROSS-REFERENCE TO RELATED APPLICATIONS

This application is a US national phase of pending International Application No. PCT/JP2021/040571 filed on Nov. 4, 2021, and now published as WO 2022/158084, which designates the United States, and claims priority from and benefit of the Japanese Patent Application No. 2021-007769 filed on Jan. 21, 2021. The disclosure of each of the above-identified patent documents is incorporated herein by reference.

TECHNICAL FIELD

The present invention relates to a decontamination device for decontaminating the inside of a clean room, an isolator device or the like and, more particularly, to a decontamination device including an ultrasonic detection means for detecting an operation of the mist circulation dispersion means.

RELATED ART

In manufacturing settings for pharmaceutical or food products or in the clinical environment such as operating rooms, the indoor working area must inevitably be kept sterile. Particularly in cases where clean rooms as a working chamber for manufacturing pharmaceutical products are decontaminated, advanced decontamination validation needs to be accomplished in accordance with Good Manufacturing Practice (GMP).

In recent years, hydrogen peroxide has widely been used (in the form of a gas or mist) to decontaminate a working chamber such as a sterile room (hereinafter referred to as a "room to be decontaminated"). Advantageously, hydrogen peroxide has a strong sterilization effect, and is inexpensively available and effectively utilized as an environmentally-friendly decontamination gas that is ultimately decomposed into oxygen and water.

The following patent document 1 describes that the decontamination effect by hydrogen peroxide is provided by a condensed film of a hydrogen peroxide solution that condenses on the surface of an object to be decontaminated. Consequently, in order to make the decontamination effect for a room to be decontaminated perfect, hydrogen peroxide may be supplied in large quantities to thicken a condensed film of the resulting hydrogen peroxide solution or provide a high concentration of the hydrogen peroxide solution.

In fact, when excessive amounts of hydrogen peroxide are supplied to a room to be decontaminated, excessive condensation occurs and each manufacturing facility, precision measuring equipment placed inside a room to be decontaminated and wall surfaces of rooms to be decontaminated are subjected to corrosion by a condensed film by the resulting high concentration of hydrogen peroxide.

After a decontamination work using hydrogen peroxide, aeration is performed with clean air to remove the residual hydrogen peroxide and condensed film inside the room to be decontaminated. However, the supply of such an excessive amount of hydrogen peroxide is problematic due to longer duration required in the aeration operation for removing a high concentration of condensed film of a hydrogen peroxide solution generated on wall surfaces and other portions of the room to be decontaminated.

In the following patent document 2, inventors of the present invention propose a decontamination device capable of accomplishing a decontamination effect with a proper amount of decontamination agent supplied to a room to be decontaminated by employing an ultrasonic mist circulation dispersion means and reducing the duration of operations such as aeration to achieve more efficient decontamination works.

CITATION LIST

Patent Literature

Patent Document 1: JP-A-61-004543
Patent Document 2: JP-A-2020-156970

SUMMARY OF THE INVENTION

Technical Problem

The above patent document 2, however, discloses the use of a plurality of ultrasonic transmitters in a mist circulation dispersion means, but no method for confirming their operations, which poses challenges for guaranteeing the overall operation as a decontamination device.

Thus, the present invention was made in view of the situation to solve the problems, and has an object to provide a decontamination device capable of confirming accurate operations of a mist circulation dispersion means before and after or during a decontamination operation and guaranteeing the overall operation as a decontamination device.

Solution to the Problem

To solve the aforementioned problem, inventors of the present invention have carried out an extended investigation to find the advantage of providing a mechanism for operating each of a plurality of ultrasonic transmitters included in a mist circulation dispersion means and an ultrasonic receiver for confirming the operation of each of the ultrasonic transmitters. Based on that technique, the present invention was accomplished.

Specifically, a decontamination device (20) according to the embodiments of the present invention includes, according to recitation in claim 1, a mist supply means (30) for converting a chemical for decontamination for decontaminating the inside of a working chamber (10, 70, 80) into a mist for decontamination and supplying the mist for decontamination to the inside of the working chamber;

a mist circulation dispersion means (40, 60*a*) for subjecting a vibrating board (41, 42, 61) including a plurality of ultrasonic transmitters (46, 51, 63) to ultrasonic vibration to generate sound flows by ultrasound from board surfaces in the vertical direction and pressing the mist for decontamination by acoustic radiation pressure of the sound flows to circulate and disperse the mist for decontamination in the working chamber; and an ultrasound detection means (60*b*) including an ultrasonic receiver (52, 65) for detecting operations of the ultrasonic transmitters to detect the operation of the plurality of ultrasonic transmitters included in the vibrating board in their entirety and/or the operation of each of the ultrasonic transmitters.

Moreover, embodiment of the present invention is, according to recitation in claim 2, the decontamination device according to claim 1, characterized in that the mist circulation dispersion means includes an operation control mechanism (62) for controlling the operation of the plurality of ultrasonic transmitters included in the vibrating board, and each of the plurality of ultrasonic transmitters can be operated to confirm each of the operations of the ultrasonic transmitters.

Furthermore, embodiment of the present invention is, according to claim 3, the decontamination device according to claim 1 or 2, characterized in that the mist circulation dispersion means includes a wave transmission control mechanism for varying the frequency and output of ultrasounds generated from the plurality of ultrasonic transmitters included in the vibrating board, and/or for transmitting ultrasounds intermittently.

Advantageous Effects of the Invention

According to the above configuration, a decontamination device according to the present invention includes a mist supply means, a mist circulation dispersion means, and an ultrasonic detection means. The mist supply means converts a chemical for decontamination for decontaminating the inside of a working chamber into a mist for decontamination and supplies the mist for decontamination to the inside of the working chamber. The mist circulation dispersion means subjects a vibrating board including a plurality of ultrasonic transmitters to ultrasonic vibration to generate sound flows by ultrasound from board surfaces in the vertical direction and presses the mist for decontamination by acoustic radiation pressure of the sound flows to circulate and disperse the mist for decontamination in the working chamber. The ultrasonic detection means includes an ultrasonic receiver for detecting operations of the ultrasonic transmitters to detect the operation of the plurality of ultrasonic transmitters included in the vibrating board in their entirety and/or the operation of each of the ultrasonic transmitters.

Accordingly, embodiments of the present invention provide a decontamination device capable of confirming accurate operations of a mist circulation dispersion means before and after or during a decontamination operation and guaranteeing the overall operation as a decontamination device.

According to the above configuration, the mist circulation dispersion means includes an operation control mechanism for controlling the operation of the plurality of ultrasonic transmitters included in the vibrating board. Accordingly, each of the plurality of ultrasonic transmitters can be operated to confirm each of the operations of the ultrasonic transmitters. Thus, the above operational advantage can more specifically and effectively be provided.

According to the above configuration, the mist circulation dispersion means includes a wave transmission control mechanism. The wave transmission control mechanism can vary the frequency and output of ultrasounds generated from the plurality of ultrasonic transmitters included in the vibrating board. Also, the wave transmission control mechanism can intermittently transmit ultrasounds generated from the plurality of ultrasonic transmitters included in the vibrating board. Thus, the above operational advantage can more specifically and effectively be provided.

BRIEF DESCRIPTION OF THE DRAWINGS

FIG. 3 (with sub-FIGS. 3(1) and 3(2)) provides conceptual diagrams showing the relationship between an ultrasonic transmitter and an ultrasonic receiver;

FIG. 5 is a conceptual diagram showing a detection operation for confirming an operation of an ultrasonic transmitter;

FIG. 6 (with sub-FIGS. 6(1) and 6(2)) provides an internal cross-sectional view showing the inside of the isolator viewed on the ceiling surface side and also a conceptual diagram showing the operation of the ultrasonic transmitter confirmed before decontamination;

FIG. 7 is a conceptual diagram showing the operation of the ultrasonic transmitter confirmed during decontamination in the internal cross-sectional view of FIG. 6; and FIG. 8 (with sub-FIGS. 8(1) and 8(2)) provides an internal cross-sectional view showing the inside of a pass box provided in conjunction with the isolator of FIG. 6 viewed on the ceiling surface side, and also a conceptual diagram showing the operations of the ultrasonic transmitter confirmed before decontamination (FIGS. 8(1)) and during decontamination FIG. 8(2).

DETAILED DESCRIPTION

In the present invention, the term "mist" is broadly interpreted as the state of a liquid droplet of a decontamination agent refined and floating in the air, the state of a gas and a liquid agent of a decontamination agent in mixture, the state of the decontamination agent to repeat the change in phase between condensation and evaporation of a gas and a droplet, and the like. In terms of particle size as well, the mist is also broadly interpreted to include mists, fogs, and liquid droplets, which can be subclassified.

Accordingly, the mist according to the present invention is categorized into a "mist" (the size may be defined as 10 μm or less) or a "fog" (the size may be defined as 5 μm or less), and a mist having a larger particle size. In the present invention, ultrasonic vibration converts even a mist, a fog and a liquid droplet sized 3 to 10 μm or more into equalized ultrafine particles 3 μm or less to provide high-level decontamination effects.

Embodiments of the decontamination device according to the idea of the present invention will be described with reference to an embodiment. Implementation of the present invention are not restricted to the following embodiment.

Figure 1:
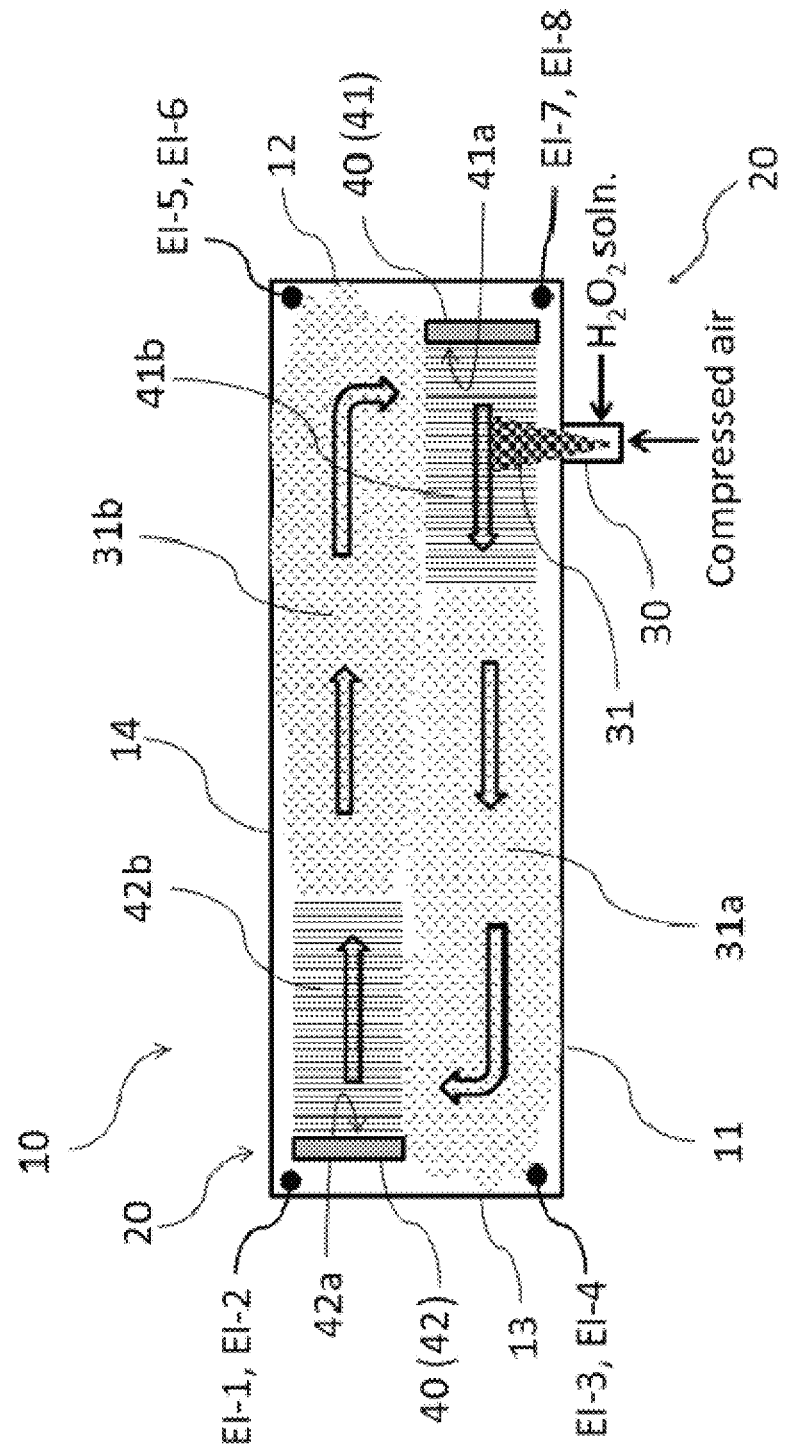
FIG. 1 is a schematic cross-sectional view showing the inside of an isolator including a decontamination device according to the invention of the patent document 2 viewed from the side.

An embodiment will be described by illustrating an isolator as a working chamber to be decontaminated. FIG. 1 is a schematic cross-sectional view showing the inside of an isolator including a decontamination device according to the invention of the above patent document 2 proposed by inventors of the present invention viewed from the side. A decontamination device according to the present invention includes not only a mist supply device and a mist circulation dispersion unit included in the decontamination device according to the invention of the above patent document 2, but also an ultrasonic detector for detecting operations of ultrasonic transmitters. The ultrasonic detector will be described in detail later.

First, the decontamination device according to the invention in the above patent document 2 will be described. In FIG. 1, an isolator 10 includes a decontamination device 20 therein. The decontamination device 20 is composed of a mist supply device 30, a mist circulation dispersion unit 40, and a first control unit (not shown). In this embodiment, the mist supply device 30 used is a two-fluid spray nozzle 30 placed on a bottom wall surface 11 of the isolator 10. In this embodiment, the decontamination agent used is a hydrogen peroxide solution ($H_2O_2$ solution).

The two-fluid spray nozzle 30 converts a hydrogen peroxide solution into a hydrogen peroxide solution mist 31 by compressed air from a compressor (not shown) to supply the same to the inside of the isolator 10. In the present invention, the mist supply device is not restricted to a two-fluid spray nozzle, and a mist generation mechanism and output are not particularly restricted.

Herein, the mist circulation dispersion unit 40 will be described. In this embodiment, the mist circulation dispersion unit 40 include 2 vibrating boards 41, 42. The 2 vibrating boards 41, 42 are disposed at 2 portions: a lower portion of a right wall surface and an upper portion of a left wall surface shown inside the isolator 10 against side wall surfaces 12, 13 such that vibrating surfaces 41a, 42a face horizontally inside the isolator 10. These 2 vibrating boards 41, 42 are arranged without allowing board surfaces (vibrating surfaces) thereof to be opposite each other (the board surfaces to face each other in front). In the present invention, instead of allowing board surfaces (vibrating surfaces) of 2 vibrating boards to be opposite each other, one or more vibrating boards may be arranged on one side of the isolator 10.

Figure 2:
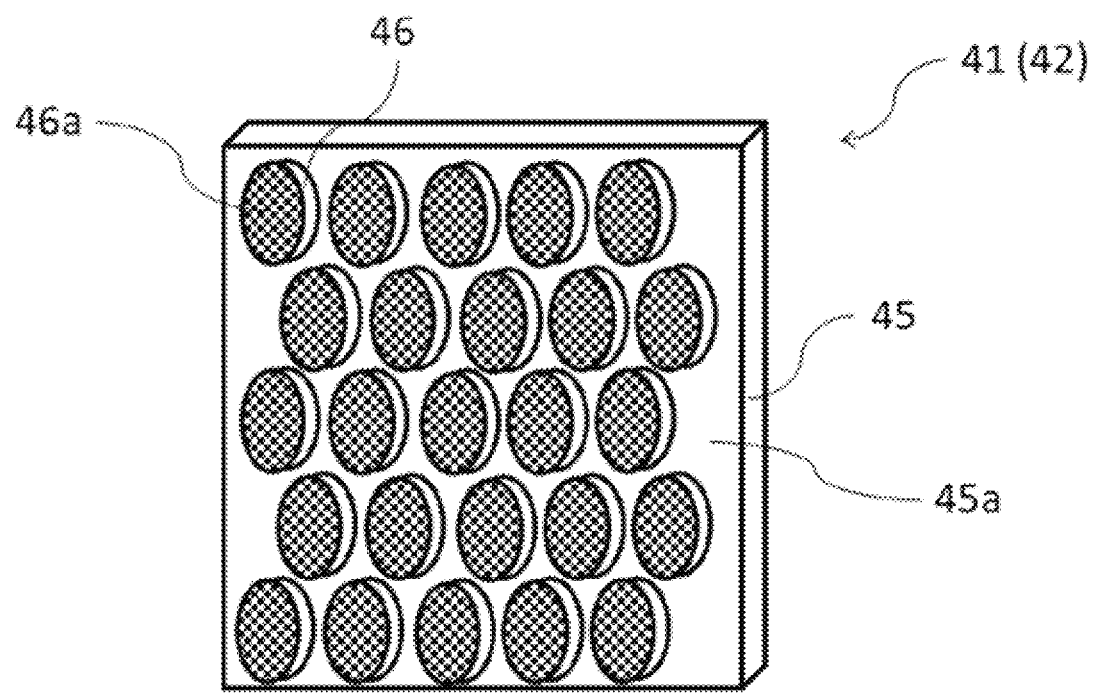
FIG. 2 is a schematic perspective view showing a plurality of ultrasonic speakers arranged in a speaker base in a vibrating board included in the decontamination device in FIG. 1.

Herein, the vibrating board 41 will be described (also applied to the vibrating board 42). FIG. 2 is a schematic perspective view showing a plurality of ultrasonic speakers (corresponding to ultrasonic transmitters) arranged in a speaker base in a vibrating board included in the decontamination device in FIG. 1. In FIG. 2, the vibrating board 41 includes a base and a plurality of ultrasonic transmitters. In the vibrating board 41 in FIG. 2, the base used is a speaker base 45, and the transmitter used is an ultrasonic speaker 46. Also, 25 ultrasonic speakers 46 are arranged on a plain surface 45a of the speaker base 45 so as to be uniform in transmission direction of a vibrating surface 46a (leftward as seen from the front shown). The number of ultrasonic speakers is not particularly restricted.

In this embodiment, the ultrasonic speaker 46 used is an ultra directional ultrasonic speaker. Specifically, an ultrasonic speaker (DC12V, 50 mA) of frequency modulation system for transmitting an ultrasound whose frequency is around 40 KHz is used. The type, size, structure and output of the ultrasonic speaker are not particularly restricted. In the present invention, the vibrating board included in the mist circulation dispersion unit is not restricted to ultrasonic speakers, and ultrasonic generation mechanisms, frequency range and output are not particularly restricted.

In this embodiment, a plurality of (25) ultrasonic speakers 46 are arranged so as to be uniform in transmission direction of the vibrating surface 46a, and the transmitters are operated in the same phase to mutually amplify ultrasounds from the plurality of ultrasonic speakers 46 in the front direction and mutually cancel out ultrasounds from the plurality of ultrasonic speakers 46 in the lateral direction. Consequently, the ultrasonic speakers 46 arranged on the speaker base 45 are subjected to ultrasonic vibration to generate a significantly directional sound flow traveling in the air from each of the vibrating surfaces 46a in the vertical direction. The frequency and output of the ultrasonic speakers 46 are controlled by a first control unit (not shown) to achieve efficient decontamination operations.

Subsequently, the action of a hydrogen peroxide solution mist 31 inside the isolator 10 including the decontamination device 20 according to the above configuration will be described. In FIG. 1, the vibrating board 41 disposed at the right lower portion shown inside the isolator 10 allows a vibrating surface 41a thereof to face in the left direction shown (in the same direction as the direction of the vibrating surface 46a of the ultrasonic speaker 46).

Ultrasonic vibration of the ultrasonic speakers 46 in the state in FIG. 1 allows a significantly directional sound flow 41b traveling in the air in the vertical direction (in the left direction shown) from the vibrating surface 41a to take in a hydrogen peroxide solution mist 31 discharged from the two-fluid spray nozzle 30, generate a pressing force by acoustic radiation pressure and move the same in the traveling direction of the sound flow 41b (in the left direction shown). The hydrogen peroxide solution mist 31 is converted into a fine mist 31a refined by ultrasonic vibration from the sound flow 41b to be circulated and dispersed inside the isolator 10.

Meanwhile, the vibrating surface 42 disposed at the left upper portion shown inside the isolator 10 allows a vibrating surface 42a thereof to face in the right direction shown (in the same direction as the direction of the vibrating surface 46a of the ultrasonic speaker 46). Ultrasonic vibration of the ultrasonic speaker 46 in this state allows a significantly directional sound flow 42b traveling in the air in the vertical direction (in the right direction shown) from the vibrating surface 42a to press the fine mist 31a refined and sent by the sound flow 41b from acoustic radiation pressure to move the same in the traveling direction of the sound flow 42b (in the right direction shown). The refined mist 31a is converted into a more stable fine mist 31b by ultrasonic vibration from the sound flow 42b to be circulated and dispersed inside the isolator 10.

Accordingly, the vibrating boards 41 and 42 are disposed inside the isolator 10 such that the respective vibrating surfaces 41a, 42a are not opposite each other in front. In cases where the vibrating surface 41a of the vibrating board 41 and the vibrating surface 42a of the vibrating board 42 are opposite each other in front, the vibrating boards 41 and 42 generate ultrasounds and their interaction generates a stationary sound wave field. This is attributed to the inability of the fine mists 31a, 31b to move due to no pressing force by acoustic radiation pressure. As described above, one or more vibrating boards may be arranged on one side of the isolator 10 to circulate a decontamination agent mist inside the isolator 10.

Thus, the fine mists 31a, 31b refined and stabilized by the sound flows 41b and 42b circulate so as to rotate in the arrow direction shown (clockwise) inside the isolator 10. The sound flows 41b and 42b, which are each a stable stationary longitudinal wave traveling on a plain surface, are transmitted as airflow having no difference in wind velocity compared to a direct type from a mist nozzle or a fan type.

In fact, since the fine mists 31a, 31b are refined by ultrasonic vibration and have smaller particle sizes and larger surface areas, it is believed that the evaporation efficiency of mists is high, resulting in repeated evaporation and condensation. The fine mists 31a, 31b are highly-refined mists to form a uniform and thin condensed film on an internal wall surface of the isolator 10. Therefore, as opposed to conventional decontamination operations, no partial, uneven or thick condensed film is formed on the internal wall surface of the isolator 10.

Thus, the fine mists 31a, 31b of hydrogen peroxide are subjected to constant ultrasonic vibration to be circulated with repeated evaporation, condensation, and refinement inside the isolator 10. Even on the internal wall surface of the isolator 10, the fine mists 31a, 31b are subjected to constant ultrasonic vibration to cause repeated re-evaporation and condensation of a uniform and thin condensed film. Accordingly, it is believed that ultrafine particles of hydrogen peroxide 3 µm or less and a hydrogen peroxide gas are subjected to phase change for coexistence inside the isolator 10 to provide a high-level decontamination environment.

Also, by repeated re-evaporation and condensation of the uniformly and thinly formed condensed film on the internal wall surface of the isolator 10, the concentration of a decontamination agent in a mist for decontamination can be increased and efficient decontamination can be performed with a small amount of decontamination agent. Such an efficient decontamination with a small amount of decontamination agent can improve the efficiency of aeration after decontamination and reduce the duration of decontamination operations. Furthermore, the secondary effect is that ultrasonic vibration and acoustic radiation pressure by the sound flows 41b and 42b can remove a deposit on the internal wall surface of the isolator 10.

Subsequently, an ultrasonic detector, which is the main technological subject of the present invention, will be described. First, an ultrasonic transmitter and an ultrasonic receiver will be described. FIG. 3 (with sub-FIGS. 3(1) and 3(2)) is a conceptual diagram showing the relationship between an ultrasonic transmitter and an ultrasonic receiver. In FIG. 3(1), a transmitting surface 51a of an ultrasonic transmitter 51 and a receiving surface 52a of an ultrasonic receiver 52 are opposite each other (the surfaces face in front).

In this state, an electric signal 51b from a first control unit (not shown) is converted into an ultrasound by the ultrasonic transmitter 51 to transmit an ultrasound 53a from the transmitting surface 51a. Subsequently, the transmitted ultrasound 53a is received on the receiving surface 52a of the ultrasonic receiver 52 and converted into an electric signal 52b. The converted electric signal 52b is recognized by a second control unit (not shown) in the ultrasonic detector to confirm an accurate operation of the ultrasonic transmitter 51.

Meanwhile, in FIG. 3(2), the transmitting surface 51a of the ultrasonic transmitter 51 and the receiving surface 52a of the ultrasonic receiver 52 are not opposite each other, but both face in the same direction to be opposite a reflecting surface 54.

In this state, an electric signal 51b from a first control unit (not shown) is converted into an ultrasound by the ultrasonic transmitter 51 to transmit an ultrasound 53a from the transmitting surface 51a. Subsequently, the transmitted ultrasound 53a is reflected on the reflecting surface 54 (may be partially attenuated) to be converted into an ultrasound 53b. Subsequently, the transmitted ultrasound 53b is received on the receiving surface 52a of the ultrasonic receiver 52 and converted into an electric signal 52b. The converted electric signal 52b is recognized by a second control unit (not shown) in the ultrasonic detector to confirm an accurate operation of the ultrasonic transmitter 51.

As described above, the ultrasonic transmitter is not restricted to an ultrasonic speaker, and it may be any type so long as it has a mechanism capable of converting an electric signal into an ultrasound. The ultrasonic receiver, which is similar in structure to the ultrasonic transmitter, may be an ultrasonic speaker. The ultrasonic receiver is not restricted to an ultrasonic speaker, and it may be any type so long as it has a mechanism capable of converting an ultrasound into an electric signal.

Subsequently, other examples of a mist circulation dispersion unit including a plurality of ultrasonic transmitters and an ultrasonic detector including an ultrasonic receiver will be described. FIG. 4 is a block diagram showing an integrated device composed of a mist circulation dispersion unit and an ultrasonic detector. In FIG. 4, a device 60 composed of a mist circulation dispersion unit 60*a* and an ultrasonic detector 60*b* in combination (hereinafter referred to as an "integrated device 60") is configured by a vibrating board 61 included in the mist circulation dispersion unit 60*a*, a first control unit 62, a plurality of ultrasonic transmitters 63 (48 units in FIG. 4), a second control unit 64 included in the ultrasonic detector 60*a*, and an ultrasonic receiver 65. The 48 ultrasonic transmitters 63 are uniformly arranged on the surface of the vibrating board 61, with one ultrasonic receiver 65 disposed in the middle position thereof. An LED pilot lamp 66 for indicating the operational state of the integrated device 60 is disposed at one end portion of the vibrating board 61.

In such a configuration, the first control unit 62 controls the operation of each of the 48 ultrasonic transmitters 63 and the operation of the 48 ultrasonic transmitters 63 in their entirety. Meanwhile, the second control unit 64 controls the operation of one ultrasonic receiver 65. In the integrated device 60, since the ultrasonic transmitters 63 and the ultrasonic receiver 65 are disposed on the same surface of the vibrating board 61, the ultrasonic receiver 65 detects reflection waves of ultrasounds transmitted by the ultrasonic transmitters 63, as described in the above FIG. 3(2). On the other hand, the ultrasonic transmitters 63 and the ultrasonic receiver 65 may be disposed at different locations to allow the ultrasonic receiver 65 to directly detect ultrasounds transmitted by the ultrasonic transmitters 63, as described in the above FIG. 3(1).

Herein, a detection operation for confirming the operation of the ultrasonic transmitters 63 will be described using the integrated device 60 according to this embodiment. FIG. 5 is a conceptual diagram showing a detection operation for confirming the operation of ultrasonic transmitters. First in FIG. 5 (Operation 1), each of the operations of all the ultrasonic transmitters before decontamination is confirmed. In consequence of Operation 1, a decontamination operation is performed after confirming the operation of all the ultrasonic transmitters. The operation of ultrasonic transmitters before the decontamination operation may be confirmed by setting thresholds for the state of operations.

Subsequently, in FIG. 5 (Operation 2), the operation of the vibrating boards (all the ultrasonic transmitters) during decontamination is confirmed. In consequence of Operation 2, a decontamination operation is performed after confirming the operation of all the ultrasonic transmitters. The decontamination operation is regarded as normally completed unless an operation stop of the vibrating boards during decontaminate is detected. In Operation 2, each of the operations of the ultrasonic transmitters is not confirmed.

Finally, in FIG. 5 (Operation 3), each of the operations of all the ultrasonic transmitters is confirmed by performing the same operation after decontamination as before decontamination. In consequence of Operation 3, the operation of the ultrasonic transmitters is regarded as normally completed even during decontamination by confirming the operations of all the ultrasonic transmitters. At this time, the operation may be confirmed by setting thresholds for the state of the operations of the ultrasonic transmitters. Thus, in Operations 1 to 3, the operations of all the ultrasonic transmitters can be confirmed to guarantee the overall operation as a decontamination device.

As for Operations 1 to 3 shown in FIG. 5, the confirmation of the operation of the ultrasonic transmitters will be described in detail. Herein, the case where 2 integrated devices 60 (see FIG. 4) are arranged on one side wall surface inside an isolator to perform a decontamination operation is illustrated, but the configuration is not restricted to that. The following description is related to the confirmation of the operation of ultrasonic transmitters, but not to a mist supply device of a decontamination device itself.

FIG. 6 (with sub-FIGS. 6(1) and 6(2)) is an internal cross-sectional view showing the inside of the isolator viewed on the ceiling surface side and also a conceptual diagram showing that the operation of the ultrasonic transmitters before decontamination is confirmed. Each of FIGS. 6(1) and 6(2) that the confirmation of the operation of the 2 integrated devices 60 is switched in the same isolator. In FIG. 6, an isolator 70 includes therein 2 integrated devices 60A, 60B arranged on one side wall surface 70a. FIG. 6 schematically shows that at a central portion inside the isolator 70, a plurality of apparatuses 71 to 77 used after decontamination are placed on a lower wall surface or suspended from a ceiling surface by a support tool 78.

Operation 1

Figure 4:
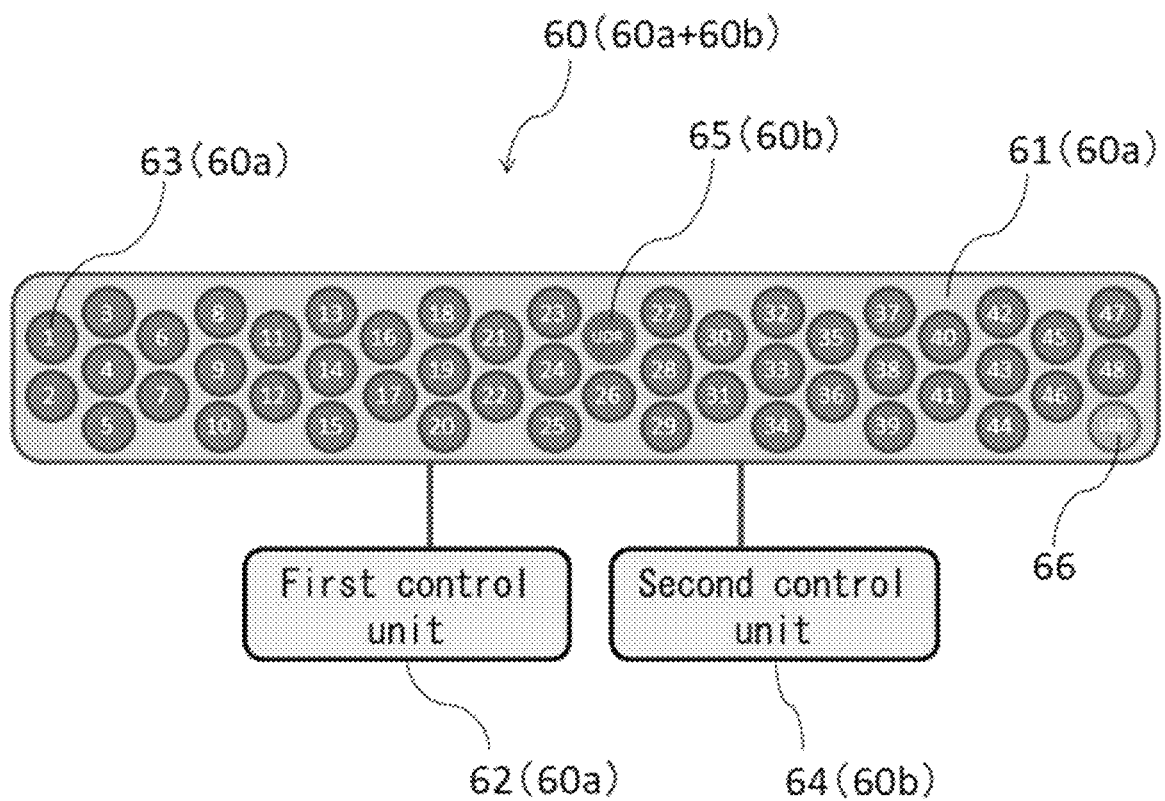
FIG. 4 is a block diagram showing an integrated device composed of a mist circulation dispersion unit and an ultrasonic detector.

In this state, first in FIG. 6 (1), the control by the first control unit 62 sequentially operates 48 ultrasonic transmitters 63 of an integrated device 60A one by one (for example, Nos. 1 to 48) (see FIG. 4). Simultaneously, the control by the second control unit 64 operates the ultrasonic receiver 65 of the integrated device 60A. In FIG. 6 (1), ultrasounds transmitted from one ultrasonic transmitter 63 are indicated by arrows. As shown in FIG. 6 (1), the transmitted ultrasounds are reflected on the surface of a plurality of apparatuses 71 to 77 and other side wall surface 70b of the isolator 70 to travel in various directions. The ultrasonic receiver 65 detects part of these reflection waves to confirm ultrasounds transmitted from one ultrasonic transmitter 63 in operation.

Accordingly, the operations of 48 ultrasonic transmitters 63 of the integrated device 60A are sequentially confirmed one by one. Meanwhile, after the operations of all the 48 ultrasonic transmitters 63 of the integrated device 60A are confirmed, the mode is subsequently switched to the integrated device 60B to confirm the operations of the 48 ultrasonic transmitters 63 (see FIG. 6 (2)). After the operations of all the ultrasonic transmitters 63 of the 2 integrated devices 60A and 60B are confirmed, the inside of the isolator 70 is decontaminated and the process will proceed to (Operation 2). At this time, the operation may be confirmed by setting thresholds for the state of the operations of the ultrasonic transmitters 63.

Operation 2

FIG. 7 is a conceptual diagram showing the operation of the ultrasonic transmitters during decontamination. In FIG. 7, 2 integrated devices 60A, 60B and a plurality of apparatuses 71 to 77 are arranged inside the isolator 70 as in FIG. 6.

In this state, a hydrogen peroxide solution mist is supplied to the inside of the isolator 70 to start decontamination. In this case, all the ultrasonic transmitters 63 of the 2 integrated devices 60A and 60B are operated to circulate and disperse the hydrogen peroxide solution mist. In FIG. 7, ultrasounds transmitted from all the ultrasonic transmitters 63 are indicated by arrows. The ultrasounds transmitted from all the ultrasonic transmitters 63 refine the hydrogen peroxide solution mist and circulates and disperses the same inside the isolator 70 for partial attenuation. As shown in FIG. 7, the attenuated ultrasounds are reflected on the surface of a plurality of apparatuses 71 to 77 and other side wall surface 70b of the isolator 70 to travel in various directions.

The ultrasonic receiver 65 for both of the 2 integrated devices 60A and 60B detects part of these reflection waves to confirm the operation of the 2 integrated devices 60A and 60B. Repeated complex reflection of the attenuated ultrasounds inside the isolator 70 thus saves the trouble of confirming the state where either of the 2 integrated devices 60A and 60B is stopped. The complex reflection also saves the trouble of confirming the state where one or more of all the ultrasonic transmitters 63 (96 units in this case) of the 2 integrated devices 60A and 60B are stopped.

That is, in (Operation 2), the state where both of the 2 integrated devices 60A and 60B are completely stopped can be confirmed. Accordingly, when both of the 2 integrated devices 60A and 60B are not completely stopped, the process will proceed to (Operation 3) as a final confirmation operation.

Operation 3

At the stage where each step of decontamination and aeration is completed, the same operation as (Operation 1) before decontamination is performed after decontamination to confirm each of the operations of all the ultrasonic transmitters 63. In cases where the above (Operation 1) and (Operation 2) can be confirmed normally and the operation of all the ultrasonic transmitters 63 of the 2 integrated devices 60A and 60B in the (Operation 3) can be confirmed, the overall operation of the integrated devices can be guaranteed as a decontamination device, and the earlier decontamination of the inside of the isolator 70 can be regarded as accurate. At this time, the operation may be confirmed by setting thresholds for the state of the operations of the ultrasonic transmitters 63.

Subsequently, the decontamination of the inside of a pass box provided in conjunction with an isolator will be described. FIG. 8 (with sub-FIGS. 8(1) and 8(2)) is an internal cross-sectional view showing the inside of a pass box provided in conjunction with the isolator viewed on the ceiling surface side, and also a conceptual diagram showing that the operation of the ultrasonic transmitters is confirmed (1) before decontamination and (2) during decontamination. In FIG. 8, the inside the pass box 80 includes therein one integrated device 60A disposed on one side wall surface 80a. FIG. 8 schematically shows that at a central portion inside the pass box 80, a plurality of apparatuses 81 to 83 are placed on a lower wall surface.

Operation 1

In this state, first in FIG. 8 (1), the control by the first control unit 62 sequentially operates 48 ultrasonic transmitters 63 of the integrated device 60A one by one (for example, Nos. 1 to 48) (see FIG. 4). Simultaneously, the control by the second control unit 64 operates the ultrasonic receiver 65 of the integrated device 60A. In FIG. 8 (1), ultrasounds transmitted from one ultrasonic transmitter 63 are indicated by arrows. As shown in FIG. 8 (1), the transmitted ultrasounds are reflected on the surface of a plurality of apparatuses 81 to 83 and other side wall surface 80b of the pass box 80 to travel in various directions. The ultrasonic receiver 65 detects part of these reflection waves to confirm ultrasounds transmitted from one ultrasonic transmitter 63 in operation.

Accordingly, the operations of 48 ultrasonic transmitters 63 of the integrated device 60A are sequentially confirmed one by one. After the operations of all the 48 ultrasonic transmitters 63 of the integrated device 60A are confirmed, the inside of the pass box 80 is decontaminated and the process will proceed to (Operation 2). At this time, the operation may be confirmed by setting thresholds for the state of the operations of the ultrasonic transmitters 63. In addition, the inside of the pass box 80 may be decontaminated in synchronization with the inside of the above isolator 70.

Operation 2

In FIG. 8 (2), one integrated device 60A and a plurality of apparatuses 81 to 83 are arranged inside the pass box 80 as in FIG. 8 (1). In this state, a hydrogen peroxide solution mist is supplied to the inside of the pass box 80 to start decontamination. In this case, all the ultrasonic transmitters 63 of the integrated device 60A are operated to circulate and disperse the hydrogen peroxide solution mist. In FIG. 8 (2), ultrasounds transmitted from all the ultrasonic transmitters 63 are indicated by arrows. The ultrasounds transmitted from all the ultrasonic transmitters 63 refine a hydrogen peroxide solution mist and circulates and disperses the same inside the pass box 80 for partial attenuation. As shown in FIG. 8 (2), the attenuated ultrasounds are reflected on the surface of a plurality of apparatuses 81 to 83 and other side wall surface 80b of the pass box 80 to travel in various directions.

The ultrasonic receiver 65 of the integrated device 60A detects part of these reflection waves to confirm the operation of the integrated device 60A. Repeated complex reflection of the attenuated ultrasounds inside the pass box 80 thus saves the trouble of confirming the state where one or more of all the ultrasonic transmitters 63 (48 units in this case) of the integrated device 60A are stopped. That is, in (Operation 2), the state where the integrated device 60A is completely stopped can be confirmed. Accordingly, when the integrated device 60A is not completely stopped, the process will proceed to (Operation 3) as a final confirmation operation.

Operation 3

At the stage where each step of decontamination and aeration is completed, the same operation as (Operation 1) before decontamination is performed after decontamination to confirm each of the operations of all the ultrasonic transmitters 63. In cases where the confirmation of the above (Operation 1) and (Operation 2) can normally be completed and the operation of all the ultrasonic transmitters 63 of the integrated device 60A in the (Operation 3) can be confirmed, the overall operation of the integrated device can be guaranteed as a decontamination device, and the earlier decontamination of the inside of the pass box 80 can be regarded as accurate. At this time, the operation may be confirmed by setting thresholds for the state of the operations of the ultrasonic transmitters 63.

As described above, according to this embodiment, the present invention can provide a decontamination device capable of confirming accurate operations of a mist circulation dispersion means before and after or during a decontamination operation and guaranteeing the overall operation as a decontamination device.

REFERENCE SIGNS LIST 10, 70 . . . Isolator, 80 . . . Pass box,
11 . . . Bottom wall surface, 12, 13, 70a, 70b, 80a, 80b . . . Side wall surface, 14 . . . Upper wall surface,
20 . . . Decontamination device, 30 . . . Mist supply device (Two-fluid spray nozzle),
31 . . . Hydrogen peroxide solution mist, 31a . . . Fine mist,
40, 60a . . . Mist circulation dispersion unit, 60, 60A, 60B . . . Integrated device,
60b . . . Ultrasonic detector, 41, 42, 61 . . . Vibrating board, 41a, 42a . . . Vibrating surface,
41b, 42b . . . Sound flow, 45 . . . Speaker base, 45a . . . Plain surface of speaker base,
46, 51, 63 . . . Ultrasonic transmitter (Ultrasonic speaker),
46a, 51a . . . Transmitting surface of ultrasonic transmitter (vibrating surface), 51b, 52b . . . Electric signal,
52, 65 . . . Ultrasonic receiver (Ultrasonic speaker),
52a . . . Receiving surface of ultrasonic receiver (vibrating surface),
53a, 53b . . . Ultrasound, 62 . . . First control unit, 64 . . . Second control unit,
66 . . . LED pilot lamp, 71 to 77, 81 to 83 . . . Apparatus,
78 . . . Support tool.

The invention claimed is:

1. A decontamination device comprising:
a mist supply means configured to convert a chemical chosen for decontamination of an inside of a working chamber of a device into a mist for decontamination and to supply the mist for decontamination to the working chamber;
a mist circulation dispersion means configured to subject a vibrating board of the device to ultrasonic vibration to generate sound flows by ultrasound from board surfaces in a vertical direction and to press the mist with acoustic radiation pressure of the sound flows to circulate and disperse the mist in the working chamber, wherein the vibrating board includes a plurality of ultrasonic transmitters; and
an ultrasound detection means including an ultrasonic receiver configured to detect an operation of the plurality of ultrasonic transmitters included in the vibrating board as a whole and/or an operation of each of individual ultrasonic transmitters.

2. The decontamination device according to claim 1, wherein
the mist circulation dispersion means includes an operation control mechanism configured to control the operation of the plurality of ultrasonic transmitters included in the vibrating board, and
each of the plurality of ultrasonic transmitters is configured to operate individually to confirm each of the operations of the constituent ultrasonic transmitters.

3. The decontamination device according to claim 1, wherein
the mist circulation dispersion means includes a wave transmission control mechanism configured to vary frequency and output of ultrasounds generated from the plurality of ultrasonic transmitters included in the vibrating board, and/or to transmit said ultrasounds intermittently.

4. The decontamination device according to claim 2, wherein
the mist circulation dispersion means includes a wave transmission control mechanism configured to vary frequency and output of ultrasounds generated from the plurality of ultrasonic transmitters included in the vibrating board, and/or to transmit said ultrasounds intermittently.

\* \* \* \* \*